– Patent Number: 4,558,061

Date of Patent: Dec. 10, 1985

[54] BRONCHOSPASMOLYTIC 1-(3-METHANESULFONAMIDO-4-HYDROXYPHENYL)-2-[(3-(4-ACYL-AMINOPHENYL)-IMIDAZOLIDIN-2-ONE-1-YL)-ALKYLAMINO]-ETHANOLS

[75] Inventors: Anton Mentrup, Mainz-Kastel; Kurt Schromm, Ingelheim am Rhein; Ernst-Otto Renth, Ingelheim am Rhein; Gojko Muacevic, Ingelheim am Rhein; Armin Fügner, Gau-Algesheim, all of Fed. Rep. of Germany

[73] Assignee: Boehringer Ingelheim KG, Ingelheim am Rhein, Fed. Rep. of Germany

[21] Appl. No.: 628,383

[22] Filed: Jul. 6, 1984

[30] Foreign Application Priority Data

Jul. 18, 1983 [DE] Fed. Rep. of Germany ....... 3325875

[51] Int. Cl.⁴ .................. A61K 31/415; C07D 233/36
[52] U.S. Cl. ..................................... 514/392; 548/320
[58] Field of Search ..................... 548/320; 424/273 R; 514/392

[56] References Cited

U.S. PATENT DOCUMENTS 4,271,158  6/1981  Mentrup et al. ................... 548/320

*Primary Examiner*—Henry R. Jiles
*Assistant Examiner*—Kurt G. Briscoe
*Attorney, Agent, or Firm*—Hammond & Littell, Weissenberger & Dippert

[57] ABSTRACT

Compounds of the formula

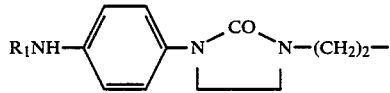
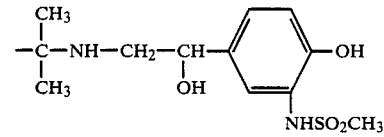

wherein n is 1 or 2,
$R_1$ is hydrogen, $-CO-R_2$ or $-SO_2R_3$,
$R_2$ is hydrogen, alkyl of 1 to 4 carbon atoms, alkoxy of 1 to 4 carbon atoms or (alkyl of 1 to 4 carbon atoms)amino, and
$R_3$ is alkyl of 1 to 4 carbon atoms, and non-toxic, pharmacologically acceptable acid addition salts thereof. The compounds as well as their salts are useful as bronchospasmolytics.

6 Claims, No Drawings

BRONCHOSPASMOLYTIC 1-(3-METHANESULFONAMIDO-4-HYDROXY-PHENYL)-2-[(3-(4-ACYL-AMINOPHENYL)-IMIDAZOLIDIN-2-ONE-1-YL)-ALKYLAMINO]-ETHANOLS

This invention relates to novel derivatives of 1-phenylimidazolidin-2-one and acid addition salts thereof, to methods of preparing these compounds, to pharmaceutical compositions containing them as active ingredients, and to a method of using them as bronchospasmolytics.

THE PRIOR ART

German Offenlegungsschrift No. 2,609,645 discloses related compounds, but they do not exhibit the favorable activity exhibited by the compounds of the present invention.

THE INVENTION

More particularly, the present invention relates to a novel class of compounds represented by the formula

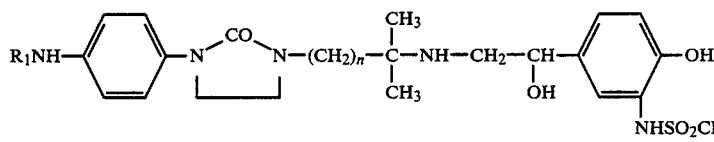

(I)

wherein
n is 1 or 2,
$R_1$ is hydrogen, —CO—$R_2$ or —$SO_2R_3$,
$R_2$ is hydrogen, alkyl of 1 to 4 carbon atoms, alkoxy of 1 to 4 carbon atoms or (alkyl of 1 to 4 carbon atoms) amino and
$R_3$ is alkyl of 1 to 4 carbon atoms,
and non-toxic, pharmacologically acceptable acid addition salts thereof.

The compounds of this invention may occur in the form of mixtures of the enantiomers or in the form of the pure enantiomers.

The alkyl and alkoxy groups mentioned in the definition of $R_2$ and $R_3$ may be straight-chained or branched. These groups preferably contain 1 to 2 carbon atoms. The group —$COR_2$ particularly represents —CHO, $CH_3CO$—, $CH_3OCO$— or $C_2H_5OCO$—, and the group $SO_2R_3$ particularly represents —$SO_2CH_3$.

The compounds embraced by formula I may be prepared by the following methods:

Method A

By reductive alkylation of a phenylglyoxal or a corresponding hemi-acetal of the formula

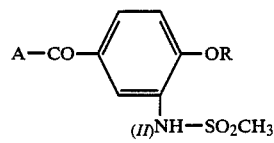

wherein:
A is —CHO or

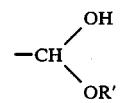

($R'$=H or $C_{1-4}$ alkyl),
and
R is a protective group which can be split off by hydrolysis or hydrogenation, with a compound of the formula (III)

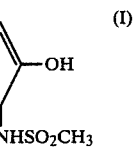

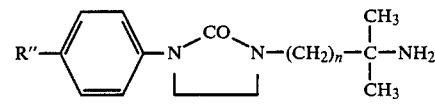

wherein
R" represents $NH_2$, $NHCOR_2$, $NHSO_2R_3$ or $NO_2$,
n represents 1 or 2.

Suitable reducing agents for the reductive alkylation include complex hydrides, preferably sodium borohydride, or hydrogen in the presence of hydrogenation catalysts such as platinum, palladium or nickel.

The protective group R may be, in particular, benzyl which is split off by hydrogenation, or an acyl group, particularly of a lower alkanoic acid, which is removed by alkaline or acid hydrolysis. The protective groups may be split off during or after the reductive alkylation.

When R" is nitro, the reduction to the amino group is effected either during the reductive alkylation or subsequently by catalytic hydrogenation.

The intermediate compound of the formula (IV)

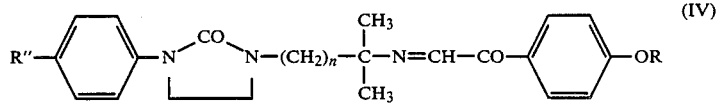

which may occur during reductive alkylation may also be isolated and then reduced.

The reaction of this method is carried out in a solvent which is inert under the reaction conditions, for instance in a lower alcohol such as methanol, ethanol or propanol. If a hydride is used as the reducing agent, cooling is preferably carried out, whereas hydrogenation may also be effected at elevated temperatures.

The starting compounds of the formulas II and III are known or may be prepared by conventional methods.

Method B

By reduction of an aminoketone of the formula

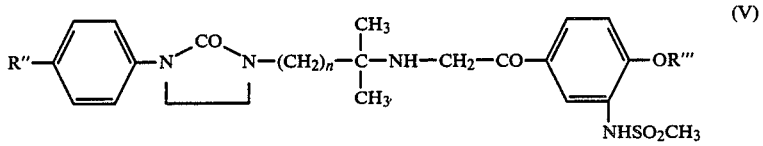

wherein:

n and R'' have the meanings previously defined, and R''' is hydrogen, —CH$_2$—aryl, —CO—(C$_{1-4}$alkyl) or —CO—aryl, where the aryl is preferably optionally substituted phenyl.

Suitable reducing agents include, for example, hydrogen and hydrogenation catalysts such as platinum, palladium, nickel or complex hydrides, particularly sodium borohydride.

When R'' is nitro, the reduction to the amino group is effected either simultaneously with the catalytic hydrogenation of the aminoketone or by catalytic hydrogenation after the reduction of the aminoketone with a hydride.

When R''' is a protective group, it is split off either during or after the reduction of the keto group. The arylmethyl group is removed by catalytic hydrogenation, and the acid group is split off by acid or alkaline hydrolysis.

The starting compounds of the formula IV may be prepared by conventional methods.

Method C

By splitting off the protective group or groups from a compound of the formula

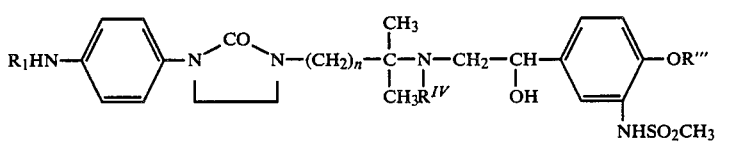

wherein n, R$_1$ and R''' have the meanings previously defined, and R$^{IV}$ is hydrogen or a group which can be split off by hydrogenation, at least one of the groups R''' and R$^{IV}$ being a group which is to be split off.

If R''' is a group removable by hydrogenation, it is removed by catalytic hydrogenation in the presence of a platinum, palladium or nickel catalyst. R$^{IV}$ is removed analogously if it is a group removable by hydrogenation. If R''' is a group removable by hydrolysis, it is split off by acid or alkaline hydrolysis.

The starting compounds of the formula VI are obtained by conventional methods.

The compounds embraced by formula I are basic and therefore form addition salts with inorganic or organic acids. Examples of non-toxic, pharmacologically acceptable acid addition salts are those formed with hydrochloric, hydrobromic, sulfuric, phosphoric, fumaric, succinic, tartaric, citric, lactic, maleic or methanesulfonic acid.

Pure enantiomers or mixtures of the enantiomers with different proportions of the antipodes may be obtained by separating racemates into their components by conventional methods, or also by using corresponding precursors.

The following examples illustrate the present invention and will enable others skilled in the art to understand it more completely. It should be understood, however, that the invention is not limited solely to the particular examples given below.

EXAMPLE 1

1-(3-Methanesulfonamido-4-hydroxyphenyl)-2-{1,1-dimethyl-3-[3-(4-acetaminophenyl)-imidazolidin-2-on-1-yl]-propylamino}-ethanol hydrochloride (a) A mixture of 35 g of 1-(4-nitrophenyl)-imidazolidin-2-one, 8.2 g of sodium hydride and 200 ml of hexametapol was mixed with a solution of 38.8 g of 3-chloro-1,1-dimethyl-1-(N-benzylideneamino)propane in 40 ml of hexametapol. The resulting mixture was heated at 100° C. for 3 hours, the solvent was removed, and after the addition of 100 ml of 2N hydrochloric acid the compound of the formula

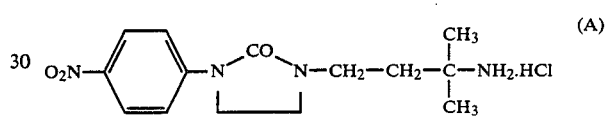

was obtained. Yield: 40 g; m.p. 288° C.

(b) To reduce the nitro group, 32.85 g of compound A were hydrogenated in 1500 ml of methanol in the presence of 0.5 g of platinum oxide at 20° C. and at 5 bar. 22.2 g of the aminophenol derivative corresponding to A were obtained in the form of the monohydrochloride (compound B; m.p. 223°–224° C.).

(c) 9 g of compound B were heated in 60 ml of glacial acetic acid with 9 ml of acetic acid anhydride at 70° C. After 10 minutes the compound of the formula

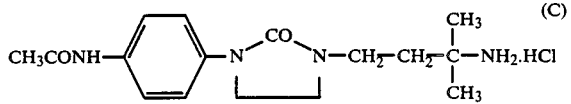

were isolated (9.5 g; m.p. 270° C.). The base, m.p. 176.5° C., was obtained from the hydrochloride by the addition of aqueous ammonia.

(d) 3.04 g of compound C were heated in 100 ml of ethanol with 4.17 g of the hemiacetal of the formula

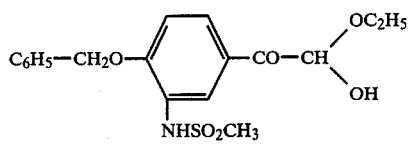

at 70° C., and after standing overnight at 15°–20° C. 1 g of sodium borohydride was added to the mixture. After stirring for three hours, the mixture was acidified with hydrochloric acid, and the isolated crude product (7.2 g) was precipitated as a salt in acetonitrile by the addition of methanesulfonic acid.

6.6 g of the compound of the formula

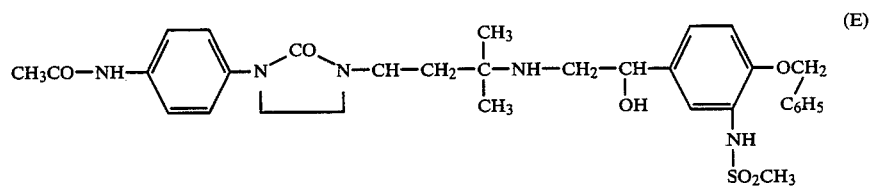

were obtained in the form of the methanesulfonate, m.p. 146° C. (compound E).

The compound of formula

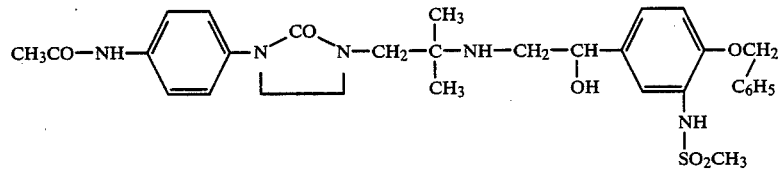

may be obtained analogously.

(e) 0.8 g of 10% palladium-on-charcoal was added to a solution of 4.2 g of compound E (as the base) in 110 ml of methanol, and the mixture was hydrogenated at 20° C. under normal pressure. After the catalyst had been removed, the solution was evaporated. The residue was recrystallized from ethanol. Yield: 3.3 g of the title compound (as base), m.p. 132° C. By adding ethereal hydrochloric acid to the methanolic solution of the base, the hydrochloride was obtained which, after crystallization with 3 mol of water, melted at 137° C.

EXAMPLE 2

1-(3-Methanesulfonamido-4-hydroxyphenyl)-2-{1,1-dimethyl-3-[3-(4-aminophenyl)imidazolidin-2-on-1-yl]-propylamino}-ethanol hydrochloride A solution of 3.7 g of 1-(3-methanesulfonamido-4-benzyloxyphenyl)-2-{1,1-dimethyl-3-[3-(4-nitrophenyl)-imidazolidin-2-on-1-yl]-propylamino}-ethanol hydrochloride in 250 ml of methanol was mixed with 0.2 g of HCl in 10 ml of methanol and, after addition of 0.7 g of 5% palladium/charcoal, the mixture was hydrogenated at 26° C. and under normal pressure. The resulting solution, freed from the catalyst, was evaporated, and the title compound was obtained with a yield of 3.3 g.

After recrystallization from methanol the melting point was 225° C.

EXAMPLE 3

1-(3-Methanesulfonamido-4-hydroxyphenyl)-2-{1,1-dimethyl-3-[3-(4-acetaminophenyl)-imidazolidin-2-on-1-yl]propylamino}-ethanol hydrochloride A solution of 0.45 g of 1-(3-methanesulfonamido-4-benzyloxyphenyl)-2-{1,1-dimethyl-3-[3-(4-aminophenyl)-imidazolidin-2-on-1-yl]-propylamino}ethanol hydrochloride in 50 ml of methanol was hydrogenated in the presence of 0.3 g of 5% palladium-on-charcoal at 25° C. and under normal pressure. 0.34 g of the title compound were obtained, m.p. 225° C. (from methanol).

The compounds listed in the following table were prepared analogously:

| Example No. | n | $R_1$ | M.p. °C. |
|---|---|---|---|
| 4 | 1 | HCO— | |
| 5 | 1 | $CH_3CO$— | |
| 6 | 1 | $C_2H_5CO$— | |
| 7 | 1 | $n\text{-}C_3H_7CO$— | |
| 8 | 1 | $(CH_3)_3CCO$— | |
| 9 | 1 | $CH_3OCO$— | |
| 10 | 1 | $C_2H_5OCO$— | |
| 11 | 1 | $i\text{-}C_3\text{—}H_7OCO$— | |
| 12 | 1 | $n\text{-}C_4H_9OCO$— | |
| 13 | 1 | $CH_3SO_2$— | |

-continued

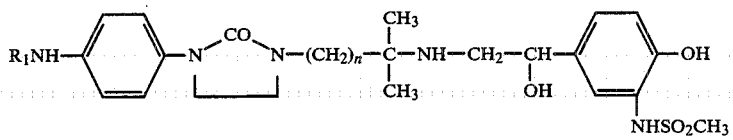

| Example No. | n | R₁ | M.p. °C. |
|---|---|---|---|
| 14 | 1 | $C_2H_5SO_2-$ | |
| 15 | 1 | $i\text{-}C_3H_7SO_2-$ | |
| 16 | 1 | $n\text{-}C_4H_9SO_2-$ | |
| 17 | 2 | $HCO-$ | |
| 18 | 2 | $C_2H_5CO-$ | |
| 19 | 2 | $n\text{-}C_3H_7CO-$ | Base 186 Hydrochloride 189 |
| 20 | 2 | $n\text{-}C_4H_9CO-$ | |
| 21 | 2 | $(CH_3)_3CCO-$ | |
| 22 | 2 | $CH_3OCO-$ | |
| 23 | 2 | $C_2H_5OCO-$ | Hydrochloride + 1 $H_2O$ 170° C. |
| 24 | 2 | $n\text{-}C_3H_7OCO-$ | |
| 25 | 2 | $(CH_3)_2-CH-CH_2OCO-$ | |
| 26 | 2 | $CH_3SO_2-$ | Hydrochloride 194° C. |
| 27 | 2 | $C_2H_5SO_2-$ | |
| 28 | 2 | $n\text{-}C_3H_7SO_2-$ | |
| 29 | 2 | $i\text{-}C_3H_7SO_2-$ | |
| 30 | 2 | $n\text{-}C_4H_9SO_2-$ | |
| 31 | 1 | H | |

The compounds of the present invention, that is, those embraced by formula I above and their non-toxic, pharmacologically acceptable acid addition salts, have useful pharmacodynamic properties. More particularly, they exhibit long-lasting bronchospasmolytic activity in warm-blooded animals, as well as vasodilating, antidepressant and cardiotonic activities. When they are used as bronchospasmolytics, their high selectivity, that is, the low effect on the heart rate, is an advantage.

For the compound of formula I wherein $R_1$ is $-COCH_3$ and n is 2, on intravenous administration for example, the $ED_{50}$ (bronchospasmolysis) in the guinea pig leads to an increase in heart rate of only about 2 beats per minute. At a higher dosage, for instance 1.0 µg/kg, the inhibition of bronchospasms produced by acetylcholine rises to 70% with a half-life of over 30 minutes, while the heart rate increases by only 10 beats per minute.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories, inhalation aerosols and the like. An effective amount of the compounds according to the present invention is from 0.014 to 7.14 mgm/kg body weight, preferably 0.028 to 2.8 mgm/kg body weight.

The following examples illustrate a few pharmaceutical compositions comprising a compound of the present invention as an active ingredient and represent the best modes contemplated of using the invention. The parts are parts by weight unless otherwise specified.

EXAMPLE 32

| | |
|---|---|
| 1-(3-Methanesulfonamido-4-hydroxyphenyl)-2-{1,1-dimethyl-3-[3-(4-acetaminophenyl)-imidazolidin-2-on-1-yl]-propylamino}- | 2 parts |

-continued

| | |
|---|---|
| ethanol hydrochloride | |
| Stearic acid | 6 parts |
| Glucose | 592 parts |
| Total | 600 parts |

The ingredients are processed in the usual way to form 600 mg-tablets.

EXAMPLE 33

Suppositories

| | |
|---|---|
| 1-(3-Methanesulfonamido-4-hydroxyphenyl)-2-{1,1-dimethyl-3-[3-(4-acetaminophenyl)-imidazolidin-2-on-1-yl]-propylamino}-ethanol hydrochloride | 100 parts |
| Powdered lactose | 45 parts |
| Cocoa butter | 1555 parts |

The ingredients are processed in the usual way to form 1.7 g-suppositories.

EXAMPLE 34

Capsules

| | |
|---|---|
| 1-(3-Methanesulfonamido-4-hydroxyphenyl)-2-{1,1-dimethyl-3-[3-(4-acetaminophenyl)-imidazolidin-2-on-1-yl]-propylamino}-ethanol hydrochloride | 10 parts |
| Lactose | 490 parts |
| Corn starch | 400 parts |

1000 mg-portions of finely powdered mixture are filled into hard gelatin capsules.

Any one of the other compounds embraced by formula I or a non-toxic, pharmacologically acceptable acid addition salt thereof may be substituted for the particular active ingredient in Examples 32 through 34. Likewise, the amount of active ingredient in these illustrative examples may be varied to achieve the dosage

We claim:

1. A compound of the formula

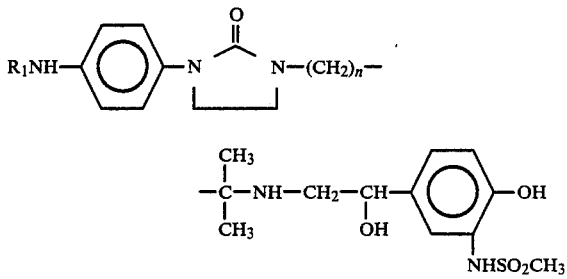

wherein n is 1 or 2, $R_1$ is —CO—$R_2$ or —$SO_2R_3$, $R_2$ is hydrogen, alkyl of 1 to 4 carbon atoms, alkoxy of 1 to 4 carbon atoms or (alkyl of 1 to 4 carbon atoms) amino, and $R_3$ is alkyl of 1 to 4 carbon atoms, an enantiomer thereof, or a nontoxic, pharmacologically acceptable acid addition salt thereof.

2. A compound of claim 1, where n is 1 or 2, $R_1$ is —CO—$R_2$, and $R_2$ is hydrogen, alkyl of 1 to 4 carbon atoms, alkoxy of 1 to 4 carbon atoms or (alkyl of 1 to 4 carbon atoms)amino, an enantiomer thereof, or a non-toxic, pharmacologically acceptable acid addition salt thereof.

3. A compound of claim 1, where n is 1 or 2, $R_1$ is —$SO_2R_3$, and $R_3$ is alkyl of 1 to 4 carbon atoms, an enantiomer thereof, or a non-toxic, pharmacologically acceptable acid addition salt thereof.

4. A compound of claim 1, which is 1-(3-methanesulfonamido-4-hydroxyphenyl)-2-{1,1-dimethyl-3-[3-(4-acetaminophenyl)-imidazolidin-2-on-1-yl]-propylamino}ethanol, an enantiomer thereof, or a non-toxic, pharmacologically acceptable acid addition salt thereof.

5. A bronchospasmolytic pharmaceutical composition consisting essentially of an inert pharmaceutical carrier and an effective bronchospasmolytic amount of a compound of claim 1.

6. The method of checking bronchospasms in a warm-blooded animal in need thereof, which comprises perorally, parenterally or rectally administering to said animal an effective bronchospasmolytic amount of a compound of claim 1.

* * * * *